US009676683B2

(12) United States Patent
Nakahara et al.

(10) Patent No.: US 9,676,683 B2
(45) Date of Patent: Jun. 13, 2017

(54) METHOD FOR PURIFYING 1,3-BUTADIENE

(71) Applicant: Asahi Kasei Chemicals Corporation, Tokyo (JP)

(72) Inventors: Tatsuto Nakahara, Tokyo (JP); Hiroshi Nakano, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 224 days.

(21) Appl. No.: 14/360,674

(22) PCT Filed: Nov. 27, 2012

(86) PCT No.: PCT/JP2012/080609
§ 371 (c)(1),
(2) Date: May 27, 2014

(87) PCT Pub. No.: WO2013/080967
PCT Pub. Date: Jun. 6, 2013

(65) Prior Publication Data
US 2015/0191403 A1 Jul. 9, 2015

(30) Foreign Application Priority Data
Nov. 28, 2011 (JP) .................. 2011-259130

(51) Int. Cl.
*C07C 7/06* (2006.01)
*C07C 7/00* (2006.01)
(Continued)

(52) U.S. Cl.
CPC ............... *C07C 7/005* (2013.01); *C07C 7/06* (2013.01); *C07C 7/10* (2013.01); *C08C 2/02* (2013.01)

(58) Field of Classification Search
CPC ......... C07C 11/167; C07C 7/005; C07C 7/10; C07C 7/06; C08C 2/02
(Continued)

(56) References Cited

U.S. PATENT DOCUMENTS 3,240,830 A * 3/1966 Dye ........................ C07C 7/12
208/188
3,663,641 A 5/1972 Hanson
(Continued)

FOREIGN PATENT DOCUMENTS

| CN | 1511811 A | 7/2004 |
| JP | S47-7321 A | 4/1972 |

(Continued)

OTHER PUBLICATIONS

Loss et al. Recovery of p-TBC from a Butadiene Washing Stream in a Pilot Plant. vol. 26 No. 4. pp. 635-640 (2009).*
(Continued)

*Primary Examiner* — Sharon Pregler
(74) *Attorney, Agent, or Firm* — Morgan, Lewis & Bockius LLP

(57) ABSTRACT

It is an object of the present invention to provide a method for purifying 1,3-butadiene which can effectively remove an organic compound detrimental to anionic polymerization from 1,3-butadiene containing a polymerization inhibitor and suppress the formation of popcorn. The method includes: a water-washing step of washing 1,3-butadiene by using low-oxygen water having an oxygen concentration of less than 2 mg/L as wash water; and a polymerization inhibitor removing step of subsequently removing the polymerization inhibitor in 1,3-butadiene.

20 Claims, 4 Drawing Sheets

(51) Int. Cl.
*C08C 2/02* (2006.01)
*C07C 7/10* (2006.01)

(58) Field of Classification Search
USPC .................................... 585/823, 824, 825
See application file for complete search history.

(56) References Cited

U.S. PATENT DOCUMENTS

| | | | |
|---|---|---|---|
| 4,547,619 A | 10/1985 | Diaz | |
| 6,174,480 B1 | 1/2001 | Nedez | |
| 6,288,299 B1* | 9/2001 | Nedez | C07B 63/00 |
| | | | 585/823 |

FOREIGN PATENT DOCUMENTS

| | | |
|---|---|---|
| JP | S55-072124 A | 5/1980 |
| JP | S61-158936 A | 7/1986 |
| JP | H08-310979 A | 11/1996 |
| JP | 2000-513007 A | 10/2000 |

OTHER PUBLICATIONS

International Preliminary Report on Patentability issued in corresponding International Patent Application No. PCT/JP2012/080609 dated Jun. 3, 2014.
European Search Report issued in related European Patent Application No. 12852999.7 dated Mar. 13, 2015.
International Search Report issued in corresponding International Patent Application No. PCT/JP2012/080609 dated Mar. 5, 2013.
Ullmann's Encyclopedia of Industrial Chemistry, 5th ed. A4: 438-439 (1985).
Shin Polymer Seizou Process (New Polymer Production Processes) (Kogyo Chosakai Publishing Co., Ltd.) 298 (1994).
Office Action issued in Taiwanese Patent Application No. 10320068090 dated Jan. 17, 2014.
International Preliminary Report on Patentability issued in corresponding International Patent Application No. PCT/JP2012/080609 dated Jun. 3, 2015.

* cited by examiner

METHOD FOR PURIFYING 1,3-BUTADIENE

TECHNICAL FIELD

The present invention relates to a method for purifying 1,3-butadiene.

BACKGROUND ART

A method for polymerizing a conjugated diene compound according to anionic polymerization in a hydrocarbon solvent or copolymerizing a conjugated diene compound and a vinyl aromatic compound has been conventionally known.

Although 1,3-butadiene is widely used as the conjugated diene, high-concentration 1,3-butadiene purified by an extractive distillation method using a specific polar solvent such as a GPB method and a BASF method from a C4 fraction obtained in naphtha cracking has been known as a petrochemical product for 1,3-butadiene (for example, see Non-Patent Literature 1).

The above-described 1,3-butadiene is apt to generate a polymer according to radical polymerization referred to as so-called popcorn, and usually contains a polymerization inhibitor such as TBC (t-butylcatechol).

Furthermore, other monomer used for copolymerization with 1,3-butadiene also contains a predetermined polymerization inhibitor.

When 1,3-butadiene and the other monomer are copolymerized, a step of removing the above-described polymerization inhibitor is required. A technique for the step of removing the polymerization inhibitor has been conventionally disclosed (for example, see Non-Patent Literature 2).

FIG. 2 shows a flow chart of a conventional step of removing a polymerization inhibitor and an impurity from 1,3-butadiene to obtain 1,3-butadiene used for anionic polymerization.

The impurity has a profound effect on a polymerization step in the anionic polymerization of 1,3-butadiene. Therefore, as shown in FIG. 2, the polymerization inhibitor is first removed, and a water-washing step is then carried out by using pure water subjected to deaeration treatment through a reduced pressure deaeration tank. A very small amount of impurity is removed by methods such as distillation and adsorption. Furthermore, a dehydrating column step, i.e., dehydrating treatment is then performed to recover 1,3-butadiene. The anionic polymerization is performed by using the 1,3-butadiene and a predetermined solvent.

CITATION LIST

Non-Patent Literature

Non-Patent Literature 1: Ullmann's Encyclopedia of Industrial Chemistry, fifth edition (1985), Vol. A4, p. 438 to 439
Non-Patent Literature 2: Shin Polymer Seizou Process (New Polymer Production Processes) (Kogyo Chosakai Publishing Co., Ltd. (published in 1994)), p. 298

SUMMARY OF INVENTION

Technical Problems to be Solved by the Invention

However, there is a possibility that the impurities in 1,3-butadiene cannot be sufficiently removed by methods such as water washing, distillation, and adsorption conventionally performed. A method for removing the impurities more efficiently is required.

Examples of the impurities may include an organic compound having active hydrogen highly likely to have an adverse effect on anionic polymerization.

Examples of the mixing situation of the organic compound having active hydrogen to 1,3-butadiene may include a situation in which a polar solvent used in extractive distillation of 1,3-butadiene serves as the organic compound having active hydrogen having an adverse effect on anionic polymerization according to a side reaction such as a hydrolysis, and the organic compound is mixed into 1,3-butadiene.

Examples of a main causative substance which may serve as the organic compound having active hydrogen may include dimethylamine and N-methyl-γ-aminobutyric acid.

Alcohols highly likely to have an adverse effect on anionic polymerization may be mixed according to various causes besides the above-described mixing situation, and other water-soluble compound may be mixed.

In view of the above, it is an object of the present invention to provide a method for purifying 1,3-butadiene which can effectively remove an organic compound detrimental to anionic polymerization of 1,3-butadiene, for example, an organic compound having active hydrogen and other water-soluble compound, and suppress the formation of popcorn.

Means For Solving the Problems

As a result of intensive studies to solve the above problems, the present inventors have found that the problems can be solved by performing a water-washing step using predetermined low-oxygen water and a polymerization inhibitor removing step, and thereby completed the present invention.

That is, the present invention is as follows.

[1]
A method for purifying 1,3-butadiene, comprising:
a water-washing step of washing 1,3-butadiene containing a polymerization inhibitor by using low-oxygen water having an oxygen concentration of less than 2 mg/L as wash water; and
a polymerization inhibitor removing step of subsequently removing the polymerization inhibitor in 1,3-butadiene.
[2]
The method for purifying 1,3-butadiene according to item [1] above, wherein a concentration of an impurity in an aqueous phase is monitored in the water-washing step.
[3]
The method for purifying 1,3-butadiene according to item [1] or [2] above, wherein the low-oxygen water is a water subjected to deoxidation treatment by using an oxygen removing film.
[4]
The method for purifying 1,3-butadiene according to any one of items [1] to [3] above, further comprising a step of heating the wash water used in the water-washing step to 60° C. or more, so as to remove 1,3-butadiene from the wash water.
[5]
The method for purifying 1,3-butadiene according to any one of items [1] to [4], further comprising a step of treating 1,3-butadiene with a deoxidant,
wherein the step of treating with the deoxidant and the polymerization inhibitor removing step are performed after the water-washing step.
[6]
The method for purifying 1,3-butadiene according to any one of items [1] to [5], further comprising a dehydrating column step of diluting 1,3-butadiene with an organic solvent, supplying the organic solvent mixed liquid of 1,3-butadiene to a dehydrating column so as to perform dehydrating treatment, and extracting the dehydrated organic solvent mixed liquid of 1,3-butadiene from a column bottom or a column intermediate part of the dehydrating column.

Advantageous Effects of Invention

The method for purifying 1,3-butadiene of the present invention can effectively remove an organic compound detrimental to anionic polymerization, for example, an organic compound having active hydrogen and other water-soluble compound, to obtain high-quality 1,3-butadiene. The method can effectively suppress the formation of popcorn in the purifying step.

MODES FOR CARRYING OUT THE INVENTION

Hereinafter, an embodiment for carrying out the present invention (hereinafter, referred to as "the present embodiment") will be described in detail. However, the present invention is not limited to contents below. The present invention can be variously modified and carried out within the scope of the gist.

[Method for Purifying 1,3-Butadiene]

A method for purifying 1,3-butadiene according to the present embodiment comprises: a water-washing step of washing 1,3-butadiene containing a polymerization inhibitor by using low-oxygen water having an oxygen concentration of less than 2 mg/L; and a polymerization inhibitor removing step of removing the polymerization inhibitor in 1,3-butadiene as the subsequent step.

Figure 1:
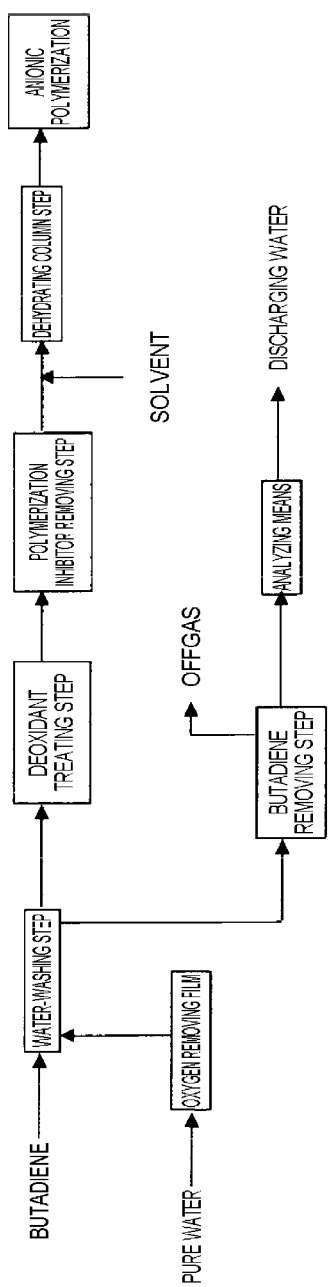
FIG. 1 shows a flow chart of an example of a step of carrying out a method for purifying 1,3-butadiene of the present embodiment.
Figure 2:
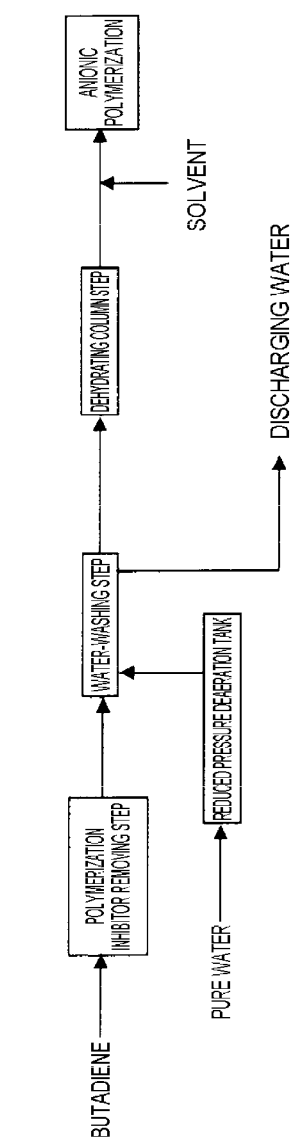
FIG. 2 shows a flow chart of a conventional purifying step of 1,3-butadiene.

FIG. 1 shows a flow chart of a step of carrying out a method for purifying 1,3-butadiene according to the present embodiment.

The flow chart of FIG. 1 is an example of a purifying step of 1,3-butadiene of the present embodiment. The present invention is not limited to the step shown in the flow chart.

(1,3-Butadiene)

1,3-Butadiene used for the purifying method according to the present embodiment is used for anionic polymerization, and previously contains a polymerization inhibitor (hereinafter, may be described as crude butadiene).

1,3-Butadiene may be pure butadiene containing 95% or more of 1,3-butadiene, obtained by various methods besides extractive distillation, crude butadiene which is a mixture of 1,3-butadiene and a C4 fraction, or a mixture thereof.

Water-Washing Step

As shown in FIG. 1, a water-washing step is first performed for the 1,3-butadiene.

The water-washing step is a step of subjecting 1,3-butadiene to water-washing treatment by using so-called low-oxygen water as wash water. The low-oxygen water is pure water having an oxygen concentration reduced to be less than 2 mg/L.

In the water-washing step, the low-oxygen water is brought into contact with 1,3-butadiene, to extract and migrate an organic compound detrimental to anionic polymerization to an aqueous phase side. A 1,3-butadiene phase and an aqueous phase are then separated from each other by separating means such as a decanter.

Figure 3:
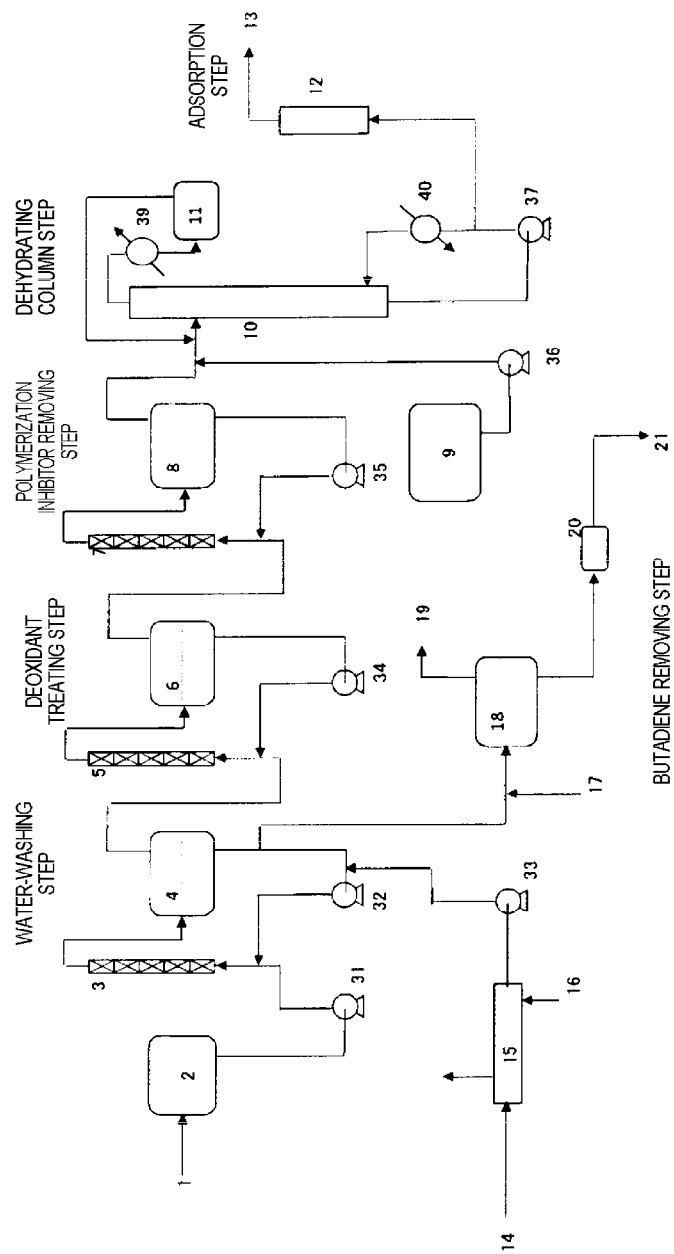
FIG. 3 shows a schematic configuration view of an apparatus for illustrating the method for purifying 1,3-butadiene.

Specifically, in FIG. 3, untreated crude 1,3-butadiene 1 is transferred to a crude 1,3-butadiene vessel 2. The crude 1,3-butadiene, low-oxygen water obtained by lowering the oxygen content of pure water 14 by an oxygen removing film apparatus 15, and low-oxygen water present in the lower layer of a decanter 4 are introduced into a liquid-liquid contact column 3 by using predetermined pumps 31 and 32. Then, these are introduced into the decanter 4, and an aqueous phase and a 1,3-butadiene phase are separated from each other in the decanter 4. In that case, an impurity is extracted to the aqueous phase.

As the wash water, the following water is used. The water is obtained by combining low-oxygen water produced by using the pure water 14 in the oxygen removing film apparatus 15 to which nitrogen 16 or the like as a deoxidation gas is supplied, and having a desired oxygen concentration, with the low-oxygen water present in the lower layer of the decanter 4, through a predetermined pipe, by using a pump 33.

In the present embodiment, the water-washing step is performed as a previous step of removing a polymerization inhibitor to be described below.

When the water-washing step is performed after a polymerization inhibitor removing step to be described below, popcorn is apt to be formed in 1,3-butadiene under the influence of a very small amount of dissolved oxygen present in water, which causes blockade trouble of a pipe or the like in the purifying step of 1,3-butadiene of the present embodiment. For this reason, in the present embodiment, the water-washing step is performed before a polymerization inhibitor removing step to be described below.

In the water-washing step, the low-oxygen water and crude 1,3-butadiene are subjected to contact treatment by a usual liquid-liquid extraction method, in the liquid-liquid contact column 3, preferably, using a static mixer, a packed column containing an irregular packing material such as a Pall ring, and a mixer with a rotary stirrer or the like. The 1,3-butadiene phase and the aqueous phase are then separated by predetermined separating means such as the decanter 4 utilizing a specific gravity difference. The decanter 4 needs to have a sufficient volume for substantially separating the butadiene phase and the aqueous phase from each other.

The residence time of the 1,3-butadiene phase in the decanter 4 is preferably 10 to 100 minutes, and more preferably 15 to 60 minutes.

The water-washing step is preferably performed at ordinary temperature under high pressure of 0.5 to 2 MpaG.

From the viewpoint of an extraction effect, a ratio of the flow rate of the low-oxygen water used in the water-washing step to the flow rate of 1,3-butadiene is preferably 1 part by mass:10 parts by mass to 10 parts by mass:1 part by mass at the flow rate of the low-oxygen water to the flow rate of 1,3-butadiene, more preferably 1 part by mass:5 parts by mass to 5 parts by mass:1 part by mass, and still more preferably 1 part by mass:3 parts by mass to 3 parts by mass:1 part by mass.

In the water-washing step, the low-oxygen water used as the wash water is preferably circulated and used. In that case, it is preferable that a part of circulating water is renewed, i.e., a part of the circulating water is discharged, and new low-oxygen water is resupplied by the amount thereof. Thereby, the amount of water to be used can be saved. The flow rate of the water to be renewed is preferably 1 to 50% by mass of the flow rate of the circulating water, and more preferably 5 to 30% by mass.

As described above, the organic compound detrimental to anionic polymerization can be effectively extracted and migrated to the aqueous phase from crude 1,3-butadiene by performing the water-washing step while circulating and utilizing the wash water at a constant flow rate ratio, and renewing a part of the wash water at a suitable flow rate. Discharging water of the same amount as that of water flow to be renewed is produced.

Examples of the organic compound having active hydrogen detrimental to anionic polymerization, and having the need for being removed in the water-washing step may include, but not limited to, amines, ammonia, carboxylic acids, alcohols, and thiols. Specific examples thereof may include secondary amines such as dimethylamine and diethylamine; primary amines such as methylamine, ethylamine, propylamine, butylamine, and 3-ethoxypropylamine; carboxylic acids such as ammonia, formic acid, acetic acid, propionic acid, acrylic acid, maleic acid, and N-methyl-γ-aminobutyric acid; alcohols such as methanol, ethanol, propanol, ethylene glycol, and propylene glycol; and thiols such as methyl mercaptan.

Furthermore, examples of other water-soluble compounds having an adverse effect on anionic polymerization, and having the necessity for being removed in the water-washing step may include, but not limited to, ketones such as acetone, and methyl ethyl ketone; aldehydes such as formaldehyde and acetaldehyde; esters such as dimethyl carbonate; and amides such as N,N-dimethylformamide, N,N-dimethylacetamide, N-methyl-2-pyrrolidone, and 1,3-dimethyl-2-imidazolidinone.

Since the above-described organic compound detrimental to anionic polymerization inactivates an anionic polymerization catalyst, and stops a polymerization reaction in some cases, it is necessary to sufficiently remove the organic compound in the water-washing step.

<Monitoring of Impurity>

In the water-washing step, it is preferable that predetermined analyzing means for analyzing an impurity in the aqueous phase is provided to monitor the impurity, i.e., the concentration of the impurity removed to the aqueous phase side is always or periodically monitored.

Specific examples thereof may include measurement of a hydrogen-ion concentration in the wash water after the above-described water-washing step, and composition analysis by gas chromatography (to be described below).

A place in which the analyzing means is provided may be a place in which the aqueous phase can be monitored, and is not particularly limited. For example, the analyzing means can be provided in an apparatus carrying out the water-washing step, preferably a discharging water pipe connected to the aqueous phase of the decanter 4 in FIG. 3. The variation state of the concentration of the impurity in 1,3-butadiene as a raw material can be detected by taking out the wash water through the pipe, removing 1,3-butadiene from the wash water, and thereafter always or periodically monitoring the wash water by using the analyzing means. A method for removing 1,3-butadiene will be described in <Discharging Water Treatment> to be described below.

As the predetermined analyzing means for analyzing the impurity in the aqueous phase, an on-line automatic measuring instrument is more preferably used. The on-line automatic measuring instrument may be an apparatus set in the pipe, and capable of always or periodically measuring a concentration automatically. Examples thereof may include a hydrogen-ion concentration measuring instrument, and a gas chromatography analysis apparatus.

The analyzing means can select various measurement forms according to impurities to be monitored.

For example, when the impurity is dimethylamine, the hydrogen-ion concentration of the wash water is preferably measured. When dimethylamine in 1,3-butadiene is increased, pH of the aqueous phase is increased after the water-washing step. Therefore, this is always monitored, and the water-washing step is carried out, and thereby dimethylamine in 1,3-butadiene can be effectively removed.

When the water-washing step is carried out after a polymerization inhibitor removing step to be described below, the wash water is taken out from the water-washing step. Furthermore, when pH is measured as the analysis of the impurity of the wash water after 1,3-butadiene is removed, the measurement of the hydrogen-ion concentration is inhibited mainly under the influence of alkali ions derived from an alkali aqueous solution used in a polymerization inhibitor removing step to be described below, which makes it difficult to sufficiently monitor the content of dimethylamine or the like which is a main impurity.

When the water-washing step is carried out after an oxygen removing step by a deoxidant to be described below, fine pH measurement is complicated under the influence of the ions of the deoxidant, which may similarly make it difficult to sufficiently monitor the content of dimethylamine or the like which is a main impurity.

Therefore, in the present embodiment, it is preferable that a polymerization inhibitor removing step to be described below is performed after the water-washing step, and the oxygen removing step by the deoxidant is also performed after the water-washing step.

When the impurities of 1,3-butadiene are alcohols, or other which cannot be measured by the hydrogen-ion concentration, the impurities can be monitored by periodically sampling the wash water and analyzing an organic substance by a gas chromatography method or the like by using predetermined analyzing means, for example, solid phase micro extraction (SPME).

When the impurities are monitored, and the increase in the impurity in 1,3-butadiene is discovered, the amount to be renewed of the low-oxygen water which is the wash water used in the water-washing step is increased, which can improve the removing efficiency of the impurity. Therefore, high-quality 1,3-butadiene is obtained, which can produce a butadiene-based polymer in a more stable polymerization step.

<Oxygen Removing Method of Wash Water Used in Water-Washing Step>

As described above, the water-washing step is performed by using the low-oxygen water obtained by removing the dissolved oxygen from the pure water, as the wash water.

A method for removing the dissolved oxygen from the pure water can be carried out by various known methods.

Examples thereof may include a method using reduced pressure means such as an ejector and a vacuum pump, a method using a deoxidant, and a method using an oxygen removing film. From the viewpoints of a stable removing effect and operation cost, the method using the oxygen removing film is preferable.

The method using the oxygen removing film is means for removing oxygen by using a semipermeable membrane not allowing water to permeate but allowing the oxygen to permeate. The method makes water flow on one side of the semipermeable membrane, and makes a gas containing substantially no oxygen, for example, nitrogen flow on the other side thereof. As the semipermeable membrane, a hollow fiber semipermeable membrane is suitably used.

An oxygen concentration in the water after the oxygen is removed is set to be less than 2 mg/L, preferably set to be 1.0 mg/L or less, and more preferably set to be 0.5 mg/L or less. The dissolved oxygen concentration is set to be less than 2 mg/L, which can effectively suppress the formation of popcorn.

<Discharging Water Treatment>

After the water-washing step is performed, the low-oxygen water used for washing, i.e., the wash water, is discharged.

When the low-oxygen water (wash water) is discharged, a step of removing 1,3-butadiene dissolved in the low-oxygen water is preferably provided.

That is, in a butadiene removing step shown in FIG. 3, the wash water separated as the aqueous phase in the decanter 4 is extracted from the decanter 4 after the water-washing step. As shown by an arrow 17, steam is added through a predetermined pipe for heating. The wash water is introduced into a 1,3-butadiene removing tank 18. Subsequently, 1,3-butadiene is removed as an offgas through a predetermined pipe as shown by an arrow 19. After 1,3-butadiene is removed as the offgas, the impurity of the wash water is analyzed by predetermined analyzing means 20. Then, as shown by an arrow 21, the wash water is discharged through a predetermined pipe. As the analyzing means, those described in the above-described <Monitoring of Impurity> can be used.

After 1,3-butadiene is removed as the offgas from the 1,3-butadiene removing tank 18, the wash water may be discharged after the wash water is analyzed by the predetermined analyzing means 20 as described above. However, the wash water may be subjected to cooling treatment by a predetermined heat exchanger, and then discharged.

Figure 4:
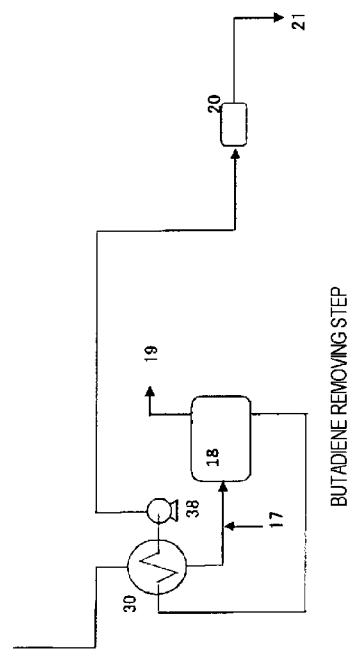
FIG. 4 shows a schematic configuration view of a main part of an apparatus for illustrating a 1,3-butadiene removing step while discharging water.

FIG. 4 shows a schematic view of a main part of an apparatus for illustrating a removing step of 1,3-butadiene in the wash water when the wash water is discharged after the wash water is subjected to cooling treatment by using a heat exchanger.

As shown in FIG. 4, 1,3-butadiene is removed as the offgas from the 1,3-butadiene removing tank 18 as shown by the arrow 19, and the wash water which is the aqueous phase is then fed into a heat exchanger 30 through a predetermined pipe. In the heat exchanger 30, the wash water is subjected to cooling treatment. The impurity of the wash water is then analyzed by the predetermined analyzing means 20 through a predetermined pump 38 and a pipe. As shown by the arrow 21, the wash water may be then discharged from a predetermined pipe.

As the method for removing 1,3-butadiene dissolved in the wash water as the offgas in the butadiene removing tank 18, a method for heating the wash water to a temperature of 60° C. or more is preferable. A method for heating the wash water to a temperature of 80° C. or more is more preferable. As heating means, any methods such as a method using a heat exchanger and a method for blowing steam can be selected.

Other examples of the method for removing 1,3-butadiene dissolved in the wash water as the offgas may include a method for lowering the total pressure of the wash water after the water-washing step as much as possible, to set the total pressure to an atmospheric pressure level or a pressure equal to or lower than the atmospheric pressure. Thereby, 1,3-butadiene can be effectively removed.

Furthermore, the above-described heating method and a method for lowering the total pressure may be carried out in combination.

According to these methods, the amount of 1,3-butadiene in the discharged water can be set to 0.1% by mass or less, and preferably 0.05% by mass or less.

In the above-described discharging water step, heat exchange is performed between low-oxygen water (wash water) to be newly supplied in order to use the low-oxygen water in the water-washing step and the wash water to be discharged, and thereby the wash water to be discharged can also be cooled with the wash water to be newly supplied.

(Polymerization Inhibitor Removing Step)

In the present embodiment, a polymerization inhibitor removing step is performed as a post step of the above-described water-washing step.

The polymerization inhibitor removing step is a step of removing a polymerization inhibitor contained in 1,3-butadiene.

The polymerization inhibitor removing step and "a step of treating using a deoxidant" (described as a deoxidant treating step in FIG. 3) to be described below may be performed with the forward/backward order of the steps exchanged. In FIG. 3, the polymerization inhibitor step is described as a post step of the deoxidant treating step. However, the polymerization inhibitor removing step may be performed before the deoxidant treating step.

In the polymerization inhibitor removing step, specifically, as shown in FIG. 3, 1,3-butadiene after the water-washing step is introduced into a liquid-liquid contact column 7 with a predetermined alkali aqueous solution. Here, the polymerization inhibitor is removed from 1,3-butadiene, and is made to migrate to the aqueous phase. Subsequently, the aqueous phase is introduced into a decanter 8 through a predetermined pipe. In the decanter 8, the polymerization inhibitor is separated from the aqueous phase. The alkali aqueous solution is circulated by a predetermined pump 35.

Examples of the polymerization inhibitor contained in 1,3-butadiene may include phenols and quinones. Among them, the phenols such as 4-tertiary-butylcatechol (TBC) and 2,6-ditertiary-butyl-p-cresol (BHT) are generally used. Of these, TBC is more general.

Examples of the method for removing the polymerization inhibitor from 1,3-butadiene may include methods such as neutralization removal using the alkali aqueous solution, adsorption removal using activated alumina or the like, and distillation. Among these, the method for performing the neutralization removal using the alkali aqueous solution is general. As the alkali, sodium hydroxide and potassium hydroxide or the like can be used. However, a method for moderately diluting a commercially available sodium hydroxide aqueous solution and using the sodium hydroxide aqueous solution is preferable. The concentration of the alkali aqueous solution is preferably 5 to 20% by mass.

Examples of the method for removing the polymerization inhibitor according to the neutralization removal using the alkali aqueous solution may include a method for putting 1,3-butadiene and an alkali aqueous solution in, preferably, a static mixer, a packed column containing an irregular packing material such as a Pall ring, and a mixer with a rotary stirrer or the like, subjecting 1,3-butadiene and the alkali aqueous solution to contact treatment according to a usual liquid-liquid extraction method for neutralization, making the polymerization inhibitor migrate to an alkali aqueous solution phase, and thereafter separating the 1,3-butadiene phase and the alkali aqueous solution phase from each other according to a specific gravity difference.

From the viewpoint of the removing effect, a ratio of the flow rate of the alkali aqueous solution to the flow rate of 1,3-butadiene is preferably 1 part by mass:10 parts by mass to 10 parts by mass:1 part by mass at the flow rate of the alkali aqueous solution to the flow rate of 1,3-butadiene, more preferably 1 part by mass:5 parts by mass to 5 parts by mass:1 part by mass, and still more preferably 1 part by mass:3 parts by mass to 3 parts by mass:1 part by mass.

In the polymerization inhibitor removing step, the alkali aqueous solution is preferably circulated and used. It is preferable that the part or whole of the alkali aqueous solution is periodically replaced and renewed.

It is preferable that the 1,3-butadiene phase and the alkali aqueous solution phase are sufficiently separated from each other. It is preferable that the residence time is sufficiently secured or the 1,3-butadiene phase and the alkali aqueous solution phase are separated from each other by two or more decanters as needed when the decanter is used. When the plurality of decanters are used, the 1,3-butadiene phase and the alkali aqueous solution phase can be sufficiently separated from each other by draining the alkali aqueous solution accumulated in the lower part in the downstream decanter.

From the viewpoint of sufficiently separating the 1,3-butadiene phase and the alkali aqueous solution phase from each other, the residence time of the 1,3-butadiene phase in the decanter is preferably 30 to 300 minutes, and more preferably 45 minutes to 100 minutes. The polymerization inhibitor removing step is preferably performed at a liquid temperature of ordinary temperature under a pressure of 0.9 to 1.1 MPaG.

(Step of Treating Using Deoxidant)

In the present embodiment, a step of treating using a deoxidant (in FIG. 3, described as a "deoxidant treating step") is preferably performed as a post step of the above-described water-washing step.

The step of treating using a deoxidant is a step of removing oxygen dissolved in 1,3-butadiene.

As described above, the "step of treating using a deoxidant" and the above-described "polymerization inhibitor removing step" may be performed with the forward/backward order of the steps exchanged. Alternatively, the step of treating using a deoxidant and the polymerization inhibitor removing step can also be simultaneously performed by adding the deoxidant to the polymerization inhibitor removing step.

Preferably, as shown in FIG. 3, the step of treating using a deoxidant is performed before the polymerization inhibitor removing step. In this case, the dissolved oxygen is more effectively removed, and such an effect is obtained that the formation of popcorn downstream can be suppressed.

Specifically, in the step of treating using a deoxidant shown in FIG. 3, 1,3-butadiene after the water-washing step is introduced into a liquid-liquid contact column 5 through a predetermined pipe with a predetermined deoxidant aqueous solution. In the liquid-liquid contact column 5, the dissolved oxygen in 1,3-butadiene is made to migrate to the deoxidant aqueous solution. The mixture is then introduced into a decanter 6 where the 1,3-butadiene phase and the aqueous phase are separated from each other. The deoxidant aqueous solution is circulated by a predetermined pump 34.

As the deoxidant, known ones which can react with dissolved oxygen in 1,3-butadiene to remove the dissolved oxygen can be used. The deoxidant is not particularly limited. Examples thereof may include sodium sulfite, sodium hydrogen sulfite, sodium hyposulfite, potassium sulfite, sodium nitrite, or a mixture containing them as a main component. From the viewpoint of a dissolved oxygen removing effect, the sodium sulfite is preferable. Examples of the mixture containing the deoxidant as a main component may include commercially available Diclean F series and Oxynon H series manufactured by Kurita Water Industries Ltd.

As described above, the deoxidant is preferably used as a form of an aqueous solution. From the viewpoints of the dissolved oxygen removing effect and economic efficiency, the concentration of the aqueous solution is preferably 3 to 30% by mass, and more preferably 5 to 20% by mass.

As the liquid-liquid contact column 5, a static mixer, a packed column containing an irregular packing material such as a Pall ring, and a mixer with a rotary stirrer or the like can be preferably used. Reaction treatment is performed according to a usual liquid-liquid contact method, and the 1,3-butadiene phase and the deoxidant aqueous solution phase are then separated from each other by separating means such as the decanter according to a specific gravity difference.

The decanter 6 needs to have a sufficient volume for substantially separating the 1,3-butadiene phase and the deoxidant aqueous solution phase from each other.

From the viewpoint of performing sufficient separation, the residence time of the 1,3-butadiene phase in the decanter 6 is preferably 10 to 100 minutes, and more preferably 15 to 60 minutes.

From the viewpoint of the dissolved oxygen removing effect, a ratio of the flow rate of the deoxidant aqueous solution to the flow rate of 1,3-butadiene is preferably 1:10 to 10 parts by mass:1 part by mass at the flow rate of the deoxidant aqueous solution to the flow rate of 1,3-butadiene, more preferably 1 part by mass:5 parts by mass to 5 parts by mass:1 part by mass, and still more preferably 1 part by mass:3 parts by mass to 3 parts by mass:1 part by mass. The deoxidant aqueous solution is preferably circulated and used. It is preferable that the part or whole of the deoxidant aqueous solution is periodically replaced and renewed.

(Dehydrating Column Step)

In the method for purifying 1,3-butadiene according to the present embodiment, a dehydrating column step is preferably performed after the above-described water-washing step, polymerization inhibitor removing step, and deoxidant treating step if needed are performed.

The dehydrating column step is a step of removing moisture dissolved in 1,3-butadiene after the water-washing step, the polymerization inhibitor removing step, and the deoxidant treating step if needed.

Specifically, 1,3-butadiene is supplied to a dehydrating column 10 with a solvent in a solvent tank 9 in the dehydrating column step shown in FIG. 3. The mixture is distilled with water from the column top of the dehydrating column 10, and cooled with a heat exchanger 39. The cooled mixture is transferred to a decanter 11, and 1,3-butadiene and the aqueous phase are then separated from each other in the decanter 11.

As described above, 1,3-butadiene is separated from the aqueous phase in the decanter 11, and then introduced into the dehydrating column 10 through a predetermined pipe. The mixed liquid of 1,3-butadiene and solvent after dehydration is distilled from the column bottom of the dehydrating column 10. A part of the mixed liquid is heated by a heat exchanger 40, and returned to the dehydrating column 10 by a pump 37. Finally, the mixed liquid of 1,3-butadiene and solvent is distilled from the column bottom by the pump 37.

In order to remove the moisture from 1,3-butadiene, dehydrating treatment is preferably performed in the dehydrating column 10 by utilizing the properties of 1,3-butadiene forming an azeotrope with water. In that case, it is preferable that 1,3-butadiene is mixed with a predetermined organic solvent before entering the dehydrating column 10, and the mixture is introduced into the dehydrating column 10. As the organic solvent, an inactive organic solvent used in a polymerization step of a polymer using 1,3-butadiene to be described below can be used. A 1,3-butadiene concentration in the mixed liquid of the organic solvent and 1,3-butadiene is preferably 20 to 70% by mass, and more preferably 30 to 60% by mass. The concentration is set to this range, and thereby dehydrating treatment operation is efficiently performed, and the formation of popcorn is suppressed.

In dehydrating column treatment, a method is preferably used, which cools and condenses a fraction distilled from the top (column top) of the dehydrating column 10, thereafter separates the aqueous phase and 1,3-butadiene from each other in the decanter 11, removes the moisture, and returns the 1,3-butadiene phase to an inlet of the dehydrating column 10 through a predetermined pipe.

A method for taking out the dehydrated 1,3-butadiene mixed liquid (the mixed solution of 1,3-butadiene and organic solvent from which the moisture is removed) from the bottom (column bottom) or middle (column intermediate part) of the dehydrating column 10 is more preferable.

When the polymerization inhibitor is sufficiently removed in the above-described polymerization inhibitor removing step, the method for taking out the dehydrated 1,3-butadiene mixed liquid from the bottom of the dehydrating column 10 is preferable. In that case, energy cost can be further decreased, and the yield of 1,3-butadiene is also good.

When the polymerization inhibitor remains in 1,3-butadiene, the entrainment of the polymerization inhibitor can be avoided by the method for extracting the dehydrated 1,3-butadiene mixed liquid from the middle (column intermediate part) utilizing the characteristics of the polymerization inhibitor having a high boiling point and condensed at the column bottom, and thereby the purity of 1,3-butadiene can be increased.

(Adsorption Step)

In the method for purifying 1,3-butadiene according to the present embodiment, it is preferable that 1,3-butadiene is further purified by an adsorption method if needed.

In the purifying according to the adsorption method, the impurity is removed by using a predetermined adsorbent.

In the adsorption step of FIG. 3, the dehydrated 1,3-butadiene mixed liquid discharged from the column bottom of the dehydrating column 10 is introduced into an adsorption column 12 where a very small amount of impurity is adsorbed and removed.

As the adsorbent, for example, activated alumina and a molecular sieve or the like can be utilized. As the adsorbent, the activated alumina is preferably used for the purpose of removing impurities such as a very small amount of polar substance, moisture, and polymerization inhibitor.

The volume of the adsorbent in the adsorption step is preferably 3 to 30 m$^3$, and more preferably 4 to 20 m$^3$.

The adsorption step is preferably used to stabilize a polymerization system for an unexpected rise of the amount of an impurity.

After the adsorption step, a purified 1,3-butadiene mixed liquid 13 is obtained.

The above-described method for purifying 1,3-butadiene according to the present embodiment can efficiently remove the organic compound having active hydrogen detrimental to anionic polymerization, particularly, the organic compound having active hydrogen such as =N—H, —O—H, and —S—H.

As the amounts of impurities in a 1,3-butadiene monomer finally obtained by the method for purifying 1,3-butadiene according to the present embodiment, the amount of dimethylamine is preferably 5 ppm or less, the amount of N-methyl-γ-aminobutyric acid is preferably 1 ppm or less, the amount of water is preferably 20 ppm or less and more preferably 10 ppm or less, and the amount of alcohols is preferably 20 ppm or less and more preferably 10 ppm or less, based on the total mass of the monomer provided for a polymerization reaction to be described below.

A small amount of a chain transfer agent for preventing gel formation during polymerization, for example, allenes and acetylenes may be present. Specifically, 1,2-butadiene, propadiene, butyne, and propyne may be present. The allenes and the acetylenes may be preferably present in an amount of 500 ppm or less based on 1,3-butadiene, more preferably 200 ppm or less, and still more preferably 100 ppm or less.

[Method for Producing Polymer Using 1,3-Butadiene]

1,3-Butadiene purified by the method for purifying 1,3-butadiene according to the present embodiment can be polymerized by using a predetermined inactive organic solvent, a monomer or monomer solution for copolymerization, a polymerization initiator, and a polymerization additive.

A polymer can be produced by using a predetermined polymerizer. The polymerizer is preferably a vessel type reactor having a stirrer.

The polymerization may be performed by a batch method or a continuous method.

After the polymer is produced, a coupling reaction and a terminal modification reaction may be performed.

Hereinafter, materials used in the polymerization step will be described.

(Materials Used for Polymerization Step)

<Monomer>

In the polymerization step, sole 1,3-butadiene purified as described above and other monomer copolymerizable with 1,3-butadiene can be used.

Examples of the other monomer copolymerizable with 1,3-butadiene may include a diene compound and an aromatic vinyl compound.

Examples of the diene compound may include, but not limited to, isoprene, 2,3-dimethyl-1,3-butadiene, 1,3-pentadiene, 3-methyl-1,3-pentadiene, 1,3-heptadiene, and 1,3-hexadiene. In particular, isoprene is preferable from the viewpoint of easiness of copolymerization.

These diene compounds may be used singly or in combinations of two or more thereof.

Examples of the aromatic vinyl compound copolymerizable with 1,3-butadiene may include, but not limited to, styrene, p-methylstyrene, α-methylstyrene, vinylethylbenzene, vinylxylene, vinylnaphthalene, and diphenylethylene. In particular, styrene is preferable.

These aromatic vinyl compounds may be used singly or in combinations of two or more thereof.

<Inactive Organic Solvent>

As the inactive organic solvent, a hydrocarbon is preferably used. A saturated hydrocarbon and an aromatic hydrocarbon or the like are used. Examples of the inactive organic solvent may include, but not limited to, aliphatic hydrocarbons such as butane, pentane, hexane, and heptane; alicyclic hydrocarbons such as cyclopentane, cyclohexane, methylcyclopentane, and methylcyclohexane; and aromatic hydrocarbons such as benzene, toluene, and xylene and hydrocarbons containing a mixture thereof.

More preferably, a solvent in which 10 to 20% by mass of hexane is mixed with cyclohexane, or mixed hexane obtained as a hexane fraction in petroleum processing can be used.

Examples of the mixed hexane may include a mixture containing normal hexane as a main component, and containing a branched hydrocarbon and an alicyclic hydrocarbon. The mixture has component rates different according to production regions of crude oils, or the like.

<Polymerization Initiator>

An alkali metal initiator can be used as the polymerization initiator.

As the alkali metal initiator, alkali metal compounds having a polymerization initiation function can be used. In particular, an organolithium compound is suitable.

Examples of the organolithium compound may include those having a low molecular weight, organolithium compounds of a solubilized oligomer, those having, in one molecule thereof, single lithium, those having, in one molecule thereof, a plurality of lithiums, and those in which an organic group and lithium are bound via a carbon-lithium bond, nitrogen-lithium bond or tin-lithium bond.

As the organolithium compound which is the alkali metal initiator, a mono-organolithium compound, a polyfunctional organolithium compound, and compounds in which an organic group and lithium are bound via a nitrogen-lithium bond can be used.

Examples of the mono-organolithium compound may include, but not limited to, n-butyllithium, sec-butyllithium, tert-butyllithium, n-hexyllithium, benzyllithium, phenyllithium, and stilbenelithium.

Examples of the polyfunctional organolithium compound may include, but not limited to, 1,4-dilithiobutane, a reaction product of sec-butyllithium and diisopropenylbenzene, 1,3,5-trilithiobenzene, a reaction product of n-butyllithium, 1,3-butadiene, and divinylbenzene, and reaction products of n-butyllithium and polyacetylene compounds.

Examples of the compounds in which an organic group and lithium are bound via a nitrogen-lithium bond may include, but not limited to, dimethylaminolithium, dihexylaminolithium, diisopropylaminolithium, and hexamethyleneiminolithium.

Furthermore, organoalkali metal compounds disclosed in U.S. Pat. No. 5,708,092, British Patent No. 2,241,239, and U.S. Pat. No. 5,527,753, or the like can also be used.

As the organolithium compound, n-butyllithium and sec-butyllithium are more preferable from the viewpoints of a polymerization initiation rate and easiness of handling.

These organolithium compounds may be used singly or in combinations of two or more thereof.

Examples of organoalkali metal compounds other than the organolithium compound may include an organosodium compound, an organopotassium compound, an organorubidium compound, and an organocesium compound.

Examples of the organoalkali metal compounds other than the organolithium compound may include, but not limited to, sodium naphthalene and potassium naphthalene. Besides, examples thereof may include alkoxides, sulfonates, carbonates, and amides of lithium, sodium, and potassium.

The alkali metal initiator may be used in combination with other organometallic compound.

Other examples of the organometallic compound may include an organomagnesium compound and an organoaluminum compound. Specific examples thereof may include dibutyl magnesium and triethyl aluminum.

<Polymerization Additive>

In the polymerization step, a polymerization additive is preferably used with the above-described polymerization initiator.

The use of the polymerization additive together with the above-described alkali metal initiator can increase a polymerization initiation rate, control the microstructure of a conjugated diene unit in the polymer, and control a monomer reactivity ratio in the copolymerization.

The polymerization additive is not limited to the following compounds. However, for example, ether compounds, tertiary amine compounds, metal alkoxide compounds, phosphine compounds, and organosulfonic acid metal compounds or the like are used. These compounds have no functional group such as active hydrogen inactivating the alkali metal initiator.

The polymerization additive has an effective randomizing effect in the copolymerization between a conjugated diene compound and an aromatic vinyl compound to be described below, and can be used as a regulating agent for regulating the distribution of the aromatic vinyl compound or the styrene block content.

Examples of the polymerization additive may include, but not limited to, ethers such as tetrahydrofuran, diethyl ether, dioxane, ethylene glycol dimethyl ether, ethylene glycol dibutyl ether, diethylene glycol dimethyl ether, diethylene glycol dibutyl ether, dimethoxybenzene and 2,2-bis(2-oxolanyl)propane; tertiary amine compounds such as tetramethylethylenediamine, dipiperidinoethane, trimethylamine, triethylamine, pyridine, and quinuclidine; alkali metal alkoxide compounds such as potassium-t-amylate, potassium-t-butylate, sodium-t-butylate, and sodium-t-amylate; phosphine compounds such as triphenylphosphine; and alkyl or arylsulfonic acid compounds such as potassium dodecylbenzene sulfonate and sodium dodecylbenzene sulfonate.

These polymerization additives may be used singly or in combinations of two or more thereof.

The amount of the polymerization additive to be used can be appropriately selected depending on the purpose and degree of effect. Usually, it is preferably 100 moles or less, and more preferably 0.01 to 10 moles per mole of the alkali metal initiator which is the above-described polymerization initiator.

(Polymerization Step)

In a predetermined polymerizer, the alkali metal initiator is used. A living polymer or a copolymer is obtained by polymerizing or copolymerizing sole 1,3-butadiene and other monomer copolymerizable with 1,3-butadiene according to solution polymerization in the inactive organic solvent.

<Polymerization Environment>

A monomer concentration in a polymerization solution is preferably 5 to 30% by mass, and more preferably 10 to 30% by mass.

The polymerization step is preferably performed with the internal temperature of the polymerizer set to 30° C. to 150° C.

If the polymerization solution contains dimethylamine as an impurity, when the concentration of the dimethylamine is set to 5 ppm or less based on 1,3-butadiene, a polymerization conversion rate and a living rate can be increased.

<Post Reaction>

The polymer or copolymer obtained in the polymerization step may be subjected to a post reaction such as a coupling reaction and a terminal modification reaction by utilizing the active terminal of the living polymer.

If the polymerization solution contains dimethylamine as the impurity in that case, when the concentration of the dimethylamine is set to 5 ppm or less based on 1,3-butadiene, the post reaction is efficiently performed.

When the coupling reaction is performed, the living polymer or living copolymer obtained in the polymerization step is reacted with a polyfunctional compound.

A compound having a plurality of functional groups in a molecule is used as the polyfunctional compound. The functional groups react with the living polymer or living copolymer to form a bond.

The polyfunctional compound has same or different functional groups having a functionality of 2 or more in a molecule, and forms a bond of at least two molecules in a coupling reaction. The polyfunctional compound forming three branches to eight branches can be used.

As a result of a bond reaction, a different functional group may be introduced into the terminal of the polymer or copolymer.

The amount of the polyfunctional compound to be used is preferably 0.05 to 5 equivalent amounts as the functional group of the polyfunctional compound based on 1 mole of the above-described alkali metal initiator, and more preferably 0.1 to 3 equivalent amounts.

Examples of the functional group reacting with the living polymer or living copolymer to form a bond may include a halogen group, a carbonyl group, a carboxylic acid ester group, a carboxylic acid amide group, a carboxylic acid halogenide group, a thiocarbonyl group, a thiocarboxylic acid ester group, a thiocarboxylic acid amide group, a thiocarboxylic acid halogenide group, an isocyanate group, a thioisocyanate group, an epoxy group, a thioepoxy group, an alkoxysilyl group, and a vinyl group and an imino group having a functional double bond.

A polyfunctional compound which has a functional group having compatibility with a packing material without being bonded to a living terminal or having bond reactivity, in the molecule of the polyfunctional compound is preferably used.

Examples of the functional group may include a tertiary amino group, and a primary or secondary amino group protected by a silicon compound.

Preferable examples of the polyfunctional compound may include tetrahalogenated silicon, bis(trihalogenated silyl) alkane, tetrahalogenated tin, tetraalkoxy silicon, trialkoxyalkyl silicon, hexaalkoxydisilane, bis(trialkoxysilyl)alkane, bis(trialkoxysilylalkyl)alkylamine, bis(trialkoxysilylalkyl) trialkylsilylamine, tris(trialkoxysilylalkyl)amine, 1,4-bis(trialkoxysilylalkyl)piperazine, 1,3-bis(trialkoxysilylalkyl)imidazolidine, 1,3-bis(trialkoxysilylalkyl) hexahydropyrimidine, 1,1-dialkoxy-2(trialkoxysilylalkyl)-1-sila-2-azacyclopentane, 1,1-dialkoxy-2 (trialkoxysilylalkyl)-1-sila-2-azacyclohexane, 1,1-dialkoxy-2(trialkoxysilylalkyl)-1-sila-2-azacycloheptane, a dicarboxylic acid diester, a tricarboxylic acid triester, a carbonic acid diester, a compound having three or more glycidyl ether groups, a compound having three or more glycidylamino groups, and a compound having two or more diglycidylamino groups.

More preferable examples of the polyfunctional compound may include a polyepoxy compound having a tertiary amino group in a molecule. Three or more epoxy groups provide a branched polymer.

In this case, a by-product is not generated. The obtained branched polymer has excellent performance as rubber.

Specific examples thereof may include tetraglycidyl-1,3-bisaminomethylcyclohexane, tetraglycidyl-meta-xylenediamine, tetraglycidyl-4,4'-diaminodiphenylmethane, N,N-diglycidyl-4-(4-glycidyl-1-piperazinyl)aniline, and N,N-diglycidyl-4-glycidyloxyaniline.

<Desolvating Step>

A polymer (copolymer) solution or a polymer (copolymer) solution oil-extended if needed is fed to a predetermined finisher by a predetermined pump or the like, to perform desolvation.

Thereby, the polymer (copolymer) which is the object is obtained.

A conventionally known method can be applied as a method for performing desolvation to obtain the polymer (copolymer).

For example, a method for separating a solvent by steam stripping or the like, thereafter filtering the solvent, further subjecting the obtained product material to anhydrating and drying treatments to obtain a polymer, a method for concentrating a solution in a flashing tank and further devolatilizing the solution using a vent extruder or the like, and a method for directly devolatilizing a solution using a drum drier or the like can be applied.

EXAMPLES

Hereinafter, the present invention will be described in detail based on specific Examples and Comparative Examples, but the present invention is not limited by the following Example.

Example 1

Water-Washing Step

A water-washing step was performed at a flow rate: 10 t/hr by using 1,3-butadiene obtained by a GPB method (ZEON process of butadiene method), containing 50 ppm of TBC (t-butylcatechol), and having a purity of 99.0% or more.

As wash water for the water-washing step, low-oxygen water treated with the following oxygen removing film apparatus was used.

<Oxygen Removing Film Apparatus, Treating Conditions of Apparatus, and Dissolved Oxygen Amount of Low-Oxygen Water>

Oxygen Removing Film Apparatus: Liqui-Cel Membrane Contactor WS-2 element size 4×28 inch membrane: ×40 Polypropylene Microporous, 25% porosity, 300 μm OD/200 μm ID Water Flow: 1 $m^3$/hr Nitrogen Flow Rate: 2.5 $m^3$/hr Dissolved Oxygen Amount in Water after Treatment: 0.3 mg/L In the water-washing step, operation was performed under conditions of a circulating water amount of 18 $m^3$/hr and a water amount to be renewed (make up) of 1 $m^3$/hr.

1,3-Butadiene and the wash water were mixed by using a static mixer (static mixer N60 series manufactured by Noritake Co., Limited), and the mixture was then transported to a decanter where a 1,3-butadiene phase and an aqueous phase were separated from each other.

The decanter was operated under conditions of a liquid temperature of 30° C. and a decanter pressure of 1.0 MPaG.

The residence time of the 1,3-butadiene phase in the decanter was 30 minutes.

The aqueous phase separated in the decanter was introduced into a 1,3-butadiene removing tank where the aqueous phase was mixed with steam and the mixture was heated to 89° C. Simultaneously, 1,3-butadiene was removed as an offgas with the total pressure set to 0.1 atmospheres G.

The remaining amount of 1,3-butadiene in discharging water after 1,3-butadiene was removed was 0.01% by mass or less.

A hydrogen-ion concentration meter as predetermined analyzing means was set in an outlet through which the aqueous phase was taken out from the 1,3-butadiene removing tank, and measured pH to monitor a concentration of an impurity.

It was found that when the concentration of dimethylamine in crude 1,3-butadiene was 0 ppm, pH of discharging water was 9. However, it was found that when pH was increased to 10, the concentration of dimethylamine in 1,3-butadiene was increased to 30 ppm.

When pH was increased to 10, the water amount to be renewed (make up) was immediately increased to 3 $m^3$/hr from 1 $m^3$/hr, to improve dimethylamine removing capability in the water-washing step. Quantitative analysis of dimethylamine in crude 1,3-butadiene was performed by a gas chromatography method according to off-line analysis.

(Oxygen Removing Step by Deoxidant)

Subsequently, a 10% aqueous solution of Diclean F-504 (manufactured by Kurita Water Industries Ltd.) containing sodium sulfite as a main component was used as a deoxidant. 1,3-Butadiene and the deoxidant aqueous solution were mixed at a circulating flow rate: 18 $m^3$/hr by using a static mixer, to perform liquid-liquid extraction. Then, the mixture was transferred to a decanter where a 1,3-butadiene phase and an aqueous phase were separated from each other.

The residence time of the 1,3-butadiene phase in the decanter was 30 minutes. The decanter was operated under conditions of a liquid temperature of 30° C. and a decanter pressure of 1.0 MPaG.

(Polymerization Inhibitor Removing Step)

Furthermore, subsequently, a 10% caustic soda aqueous solution was mixed with 1,3-butadiene at a circulating flow rate: 18 $m^3$/hr by using a packed column containing a Pall ring, to perform liquid-liquid extraction. The mixture was further transferred to other decanter where a 1,3-butadiene phase and an aqueous phase were separated from each other.

The residence time of the 1,3-butadiene phase in the other decanter was 80 minutes. In a polymerization inhibitor removing step, the decanter was operated under conditions of a liquid temperature of 30° C., and a decanter pressure of 1.0 MPaG.

(Dehydrating Column Step)

Mixed hexane was added to the 1,3-butadiene phase separated in the other decanter. The mixture was supplied to a dehydrating column with the 1,3-butadiene concentration of the mixture set to 50% by mass.

An azeotropic mixture of 1,3-butadiene and water distilled from the top (column top) in the dehydrating column was cooled and condensed. The azeotropic mixture was then transported to the decanter where a 1,3-butadiene phase and an aqueous phase were separated from each other.

The aqueous phase was removed, and the 1,3-butadiene phase was returned to a column inlet of the dehydrating column. A dehydrating column step was continuously performed.

The dehydrated mixed liquid of 1,3-butadiene and hexane was taken out from the bottom (column bottom) of the dehydrating column.

(Adsorption Step)

The mixed liquid of 1,3-butadiene and hexane was passed through a desiccant dryer (a vertical type cylindrical tank manufactured by Hitachi, Ltd.) of 9 $m^3$ containing activated alumina, to adsorb and remove a very small amount of remaining impurity in 1,3-butadiene.

(Anionic Polymerization)

The hexane mixed liquid of 1,3-butadiene obtained by purifying according to the method, hexane, and styrene were used. Batch polymerization was performed by using n-butyllithium as a polymerization initiator and 2,2-bis(2-oxolanyl)propane as a polymerization additive.

When the polymerization temperature arrived at the top, tetraglycidyl-1,3-bisaminomethylcyclohexane which was a tetra-functional coupling denaturant was added for reaction.

(Results)

The method for purifying 1,3-butadiene according to Example 1 could correctly monitor an increase in the amount of dimethylamine which was an organic compound having active hydrogen highly likely to have an adverse effect on anionic polymerization in 1,3-butadiene, and could easily control setting of appropriate conditions such as an increase in the amount to be renewed of the low-oxygen water which was the wash water in the water-washing step even when the amount of dimethylamine was increased. Thereby, high-quality 1,3-butadiene was obtained, and a polymer obtained by using this also had a structure lying within a predetermined quality standard value.

Popcorn of 1,3-butadiene in the purifying step was hardly formed at all after operation for one year.

Comparative Example 1

Polymerization Inhibitor Removing Step

A polymerization inhibitor removing step was performed at a flow rate: 10 t/hr by using 1,3-butadiene obtained by a GPB method, containing 50 ppm of TBC (t-butylcatechol), and having a purity of 99.0%.

A 10% caustic soda aqueous solution was mixed with the 1,3-butadiene at a circulating flow rate: 18 $m^3$/hr by using a packed column containing a Pall ring, to perform liquid-liquid extraction. The mixture was then transferred to a decanter where a 1,3-butadiene phase and an aqueous phase were separated from each other.

The residence time of the 1,3-butadiene phase in the decanter was 30 minutes. The decanter was operated under conditions of a liquid temperature of 30° C., and a decanter pressure of 1.0 MPaG.

(Water-Washing Step)

Subsequently, a water-washing step of 1,3-butadiene separated in the decanter was performed.

Low-oxygen water treated under a reduced pressure of 50 mmHg (abs) by using a steam ejector as a reduced pressure deaerator was used as wash water. A dissolved oxygen amount in the water after treatment was 0.7 mg/L.

The water-washing step was performed under conditions of a circulating water amount of 18 $m^3$/hr and a water amount to be renewed (make up) of 1 $m^3$/hr.

1,3-Butadiene and the wash water were mixed by using a static mixer (static mixer N60 series manufactured by Noritake Co., Limited), and the mixture was then transported to a decanter where a 1,3-butadiene phase and an aqueous phase were separated from each other. The decanter was operated under conditions of a liquid temperature of 30° C. and a decanter pressure of 1.0 MPaG. The residence time of the 1,3-butadiene phase in the decanter was 30 minutes.

Next, in the same manner as in the above-described Example 1, the aqueous phase separated in the decanter was introduced into a 1,3-butadiene removing tank where the aqueous phase was mixed with steam and the mixture was heated to 89° C. Simultaneously, 1,3-butadiene was removed with the total pressure set to 0.1 atmospheres G.

A hydrogen-ion concentration meter as predetermined analyzing means was set in a discharging water outlet pipe of the 1,3-butadiene removing tank, and measured pH of the aqueous phase after 1,3-butadiene was removed, to monitor a concentration of an impurity.

When the concentration of dimethylamine in crude 1,3-butadiene was 0 ppm, pH of discharging water was 10. However, even when the concentration of dimethylamine in 1,3-butadiene was increased to 30 ppm, pH was constant at 10. This is presumed to be because the caustic soda used in the polymerization inhibitor removing step was mixed in the discharging water in the water-washing step, which caused lacked accuracy in the indication of a discharging water pH meter.

When the hydrogen-ion concentration meter was directly set for the aqueous phase separated in the decanter without being passed through the 1,3-butadiene removing tank, air bubbles of butadiene adhered to the hydrogen-ion concentration meter, and normal measurement could not be performed.

(Dehydrating Column Step)

After the water-washing step was performed as described above, 1,3-butadiene separated from the aqueous phase in the decanter was supplied to a dehydrating column without diluting the 1,3-butadiene with a solvent.

An azeotropic mixture of 1,3-butadiene and water distilled from the top (column top) in the dehydrating column was cooled and condensed. The azeotropic mixture was then transported to the decanter where the 1,3-butadiene phase and the aqueous phase were separated from each other. The aqueous phase was removed, and the 1,3-butadiene phase was returned to a column inlet of the dehydrating column. A dehydrating column step was continuously performed.

Dehydrated 1,3-butadiene was taken out from the bottom (column bottom) of the dehydrating column.

(Anionic Polymerization)

Batch polymerization was performed in the same manner as in Example 1 by using 1,3-butadiene obtained by purifying according to the method.

When the polymerization temperature arrived at the top, tetraglycidyl-1,3-bisaminomethylcyclohexane which was a tetra-functional coupling denaturant was added for reaction.

(Results)

Since the method for purifying 1,3-butadiene according to Comparative Example 1 could not monitor an increase in the amount of dimethylamine in raw material butadiene, operation was forced to be performed in a state where the amount of water to be renewed for water washing was constant.

Therefore, even when the amount of dimethylamine which was the impurity in 1,3-butadiene was increased, dimethylamine could not be sufficiently removed in Comparative Example 1, and 1,3-butadiene having practically sufficient quality was not obtained. When a polymerization step was performed by using this, a molecular weight and a coupling rate were decreased, and the polymerization could not be correctly controlled. The obtained polymer had a structure lying outside a predetermined quality standard value.

Popcorn of butadiene was clogged in the pipe of the water-washing step, and it was necessary to remove the popcorn in a state where the operation was temporarily stopped after four months.

Comparison Between Example 1 and Comparative Example 1

In Example 1, the water-washing step was performed as a preceding step of the polymerization inhibitor removing step, and thereby the increase in dimethylamine which was the impurity in 1,3-butadiene could be monitored, and dimethylamine could be appropriately removed, which could provide high-quality 1,3-butadiene. Furthermore, the popcorn was not formed, and the operation could be stably performed in the polymerization step for a long period of time.

On the other hand, in Comparative Example 1, the water-washing step was performed after the polymerization inhibitor removing step, and thereby the measurement of the hydrogen-ion concentration was inhibited under the influence of alkali ions, and dimethylamine could not be analyzed and monitored according to pH measurement. Dimethylamine could not be suitably removed. Therefore, high-quality 1,3-butadiene was not obtained, which had a significant impact on anionic polymerization using this. Furthermore, the popcorn was formed in the producing step, and the operation was forced to be temporarily stopped.

INDUSTRIAL APPLICABILITY

A method for purifying 1,3-butadiene according to the present invention has industrial applicability as a technique of purifying 1,3-butadiene used for producing a conjugated diene polymer constituting a preferable rubber composition for tire rubber, antivibration rubber, and footwear or the like.

REFERENCE SIGN LIST

1: crude 1,3-butadiene
2: crude 1,3-butadiene vessel
3: liquid-liquid contact column
4: decanter
5: liquid-liquid contact column
6: decanter
7: liquid-liquid contact column
8: decanter
9: solvent vessel
10: dehydrating column
11: decanter
12: adsorption column
13: purified 1,3-butadiene mixed liquid
14: pure water
15: oxygen removing film apparatus
16: nitrogen
17: steam
18: 1,3-butadiene removing tank
19: offgas
20: predetermined analyzing means
21: discharging water
30, 39, 40: heat exchanger
31 to 38: pump

The invention claimed is:
1. A method of purifying 1,3-butadiene, comprising:
   washing a 1,3-butadiene stream comprising 1,3-butadiene and a polymerization inhibitor in a water-washing step by using low-oxygen water having an oxygen concentration of less than 2 mg/L as wash water; and subsequently removing the polymerization inhibitor from the 1,3-butadiene stream in a polymer inhibitor removing step thereby obtaining a purified 1,3-butadiene stream.

2. The method of purifying 1,3-butadiene according to claim 1, further comprising monitoring a concentration of an impurity in an aqueous phase in the water-washing step.

3. The method of purifying 1,3-butadiene according to claim 1, comprising subjecting water to an oxygen removing film in a deoxidation treatment to obtain the low-oxygen water.

4. The method of purifying 1,3-butadiene according to claim 1, further comprising heating the wash water used in the water-washing step to 60° C. or more, so as to remove 1,3-butadiene from the wash water.

5. The method of purifying 1,3-butadiene according to claim 1, further comprising treating 1,3-butadiene with a deoxidant,
wherein the step of treating with the deoxidant and the polymerization inhibitor removing step are performed after the water-washing step.

6. The method of purifying 1,3-butadiene according to claim 1, further comprising
diluting the 1,3-butadiene stream with an organic solvent to obtain an mixed liquid of 1,3-butadiene and organic solvent,
supplying the mixed liquid of 1,3-butadiene and organic solvent to a dehydrating column dehydrating the mixed liquid,
extracting the dehydrated mixed liquid of 1,3-butadiene from a column bottom or a column intermediate part of the dehydrating column, and
removing solvent from the mixed liquid stream thereby obtaining the purified 1,3-butadiene stream.

7. The method of purifying 1,3-butadiene according to claim 1, wherein the low-oxygen water has an oxygen concentration of less than 1 mg/L.

8. The method of purifying 1,3-butadiene according to claim 1, wherein the low-oxygen water has an oxygen concentration of less than 0.5 mg/L.

9. The method of purifying 1,3-butadiene according to claim 3, wherein the wash water used in the water-washing step is heated to 80° C. or more.

10. The method of purifying 1,3-butadiene according to claim 5, wherein the deoxidant is selected from the group consisting of sodium sulfite, sodium hydrogen sulfite, sodium hyposulfite, potassium sulfite, sodium nitrite, and a mixture thereof.

11. The method of purifying 1,3-butadiene according to claim 5, wherein the deoxidant is in an aqueous solution.

12. A method of purifying 1,3-butadiene comprising:
washing a stream comprising 1,3-butadiene and a polymerization inhibitor in a water-washing step by using low-oxygen water having an oxygen concentration of less than 2 mg/L as wash water and monitoring a concentration of an impurity in an aqueous phase;
subsequently removing the polymerization inhibitor from the stream in a polymerization inhibitor removing step to obtain a 1,3-butadiene stream;
treating the 1,3-butadiene stream comprising 1,3-butadiene with a deoxidant to obtain a treated 1,3-butadiene stream;
diluting the treated 1,3-butadiene stream with an organic solvent to obtain an mixed liquid of 1,3-butadiene and organic solvent,
supplying the mixed liquid of 1,3-butadiene and organic solvent to a dehydrating column dehydrating the mixed liquid,
extracting the dehydrated mixed liquid of 1,3-butadiene from a column bottom or a column intermediate part of the dehydrating column, and
removing solvent from the mixed liquid stream thereby obtaining a purified 1,3-butadiene stream.

13. The method of purifying 1,3-butadiene according to claim 12, comprising subjecting water to an oxygen removing film in a deoxidation treatment to obtain the low-oxygen water.

14. The method of purifying 1,3-butadiene according to claim 12, further comprising heating the wash water used in the water-washing step to 60° C. or more, so as to remove 1,3-butadiene from the wash water.

15. The method of purifying 1,3-butadiene according to claim 12, wherein the step of treating with the deoxidant and the polymerization inhibitor removing step are performed after the water-washing step.

16. The method of purifying 1,3-butadiene according to claim 12, wherein the low-oxygen water has an oxygen concentration of less than 1 mg/L.

17. The method of purifying 1,3-butadiene according to claim 12, wherein the low-oxygen water has an oxygen concentration of less than 0.5 mg/L.

18. The method of purifying 1,3-butadiene according to claim 13, wherein the wash water used in the water-washing step is heated to 80° C. or more.

19. The method of purifying 1,3-butadiene according to claim 12, wherein the deoxidant is selected from the group consisting of sodium sulfite, sodium hydrogen sulfite, sodium hyposulfite, potassium sulfite, sodium nitrite, and a mixture thereof.

20. The method of purifying 1,3-butadiene according to claim 12, wherein the deoxidant is in an aqueous solution.

* * * * *